US010913698B2

(12) United States Patent
Castillo-Welter et al.

(10) Patent No.: US 10,913,698 B2
(45) Date of Patent: Feb. 9, 2021

(54) PROCESS FOR CONDUCTING EXOTHERMIC EQUILIBRIUM REACTIONS

(71) Applicant: L'Air Liquide, Societe Anonyme pour l'Etude et l'Exploitation des Procedes Georges Claude, Paris (FR)

(72) Inventors: Frank Castillo-Welter, Friedrichsdorf (DE); Stephane Haag, Frankfurt am Main (DE); Robert Frind, Kreischa (DE); Timm Schuhmann, Offenbach (DE); Andreas Ochs, Bad Homburg (DE); Marc Wagner, Saint Maur des Fosses (FR); Solene Valentin, Le Pecq (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/612,537

(22) PCT Filed: Apr. 26, 2018

(86) PCT No.: PCT/EP2018/025131
§ 371 (c)(1),
(2) Date: Nov. 11, 2019

(87) PCT Pub. No.: WO2018/206155
PCT Pub. Date: Nov. 15, 2018

(65) Prior Publication Data
US 2020/0199054 A1 Jun. 25, 2020

(30) Foreign Application Priority Data
May 12, 2017 (EP) .................................. 17400025

(51) Int. Cl.
*B01J 8/04* (2006.01)
*B01J 19/24* (2006.01)
(Continued)

(52) U.S. Cl.
CPC ............ *C07C 29/152* (2013.01); *B01J 8/0438* (2013.01); *B01J 8/0457* (2013.01); *B01J 8/0496* (2013.01);
(Continued)

(58) Field of Classification Search
CPC ......... B01J 8/00; B01J 8/02; B01J 8/04; B01J 8/0403; B01J 8/0423; B01J 8/0438;
(Continued)

(56) References Cited

U.S. PATENT DOCUMENTS 4,326,041 A 4/1982 Bahnisch
5,631,302 A 5/1997 Konig et al.
(Continued)

FOREIGN PATENT DOCUMENTS

CN 106 380 376 2/2017
CN 106 518 609 3/2017
(Continued)

OTHER PUBLICATIONS

Ullmann's Encyclopedia of Industrial Chemistry, Sixth Edition, 1998 Electronic Release, vol. 21, "Methanol" chapter, sub-chapter 5.2 "Synthesis," pp. 620-621.
(Continued)

*Primary Examiner* — Natasha E Young
(74) *Attorney, Agent, or Firm* — Justin K. Murray

(57) ABSTRACT

A process for conducting exothermic equilibrium reactions, especially for the performance of methanol synthesis by heterogeneously catalysed conversion of synthesis gas, is proposed, which enables readjustment and hence optimization of the reaction conditions along the longitudinal coor-
(Continued)

Figure 1:
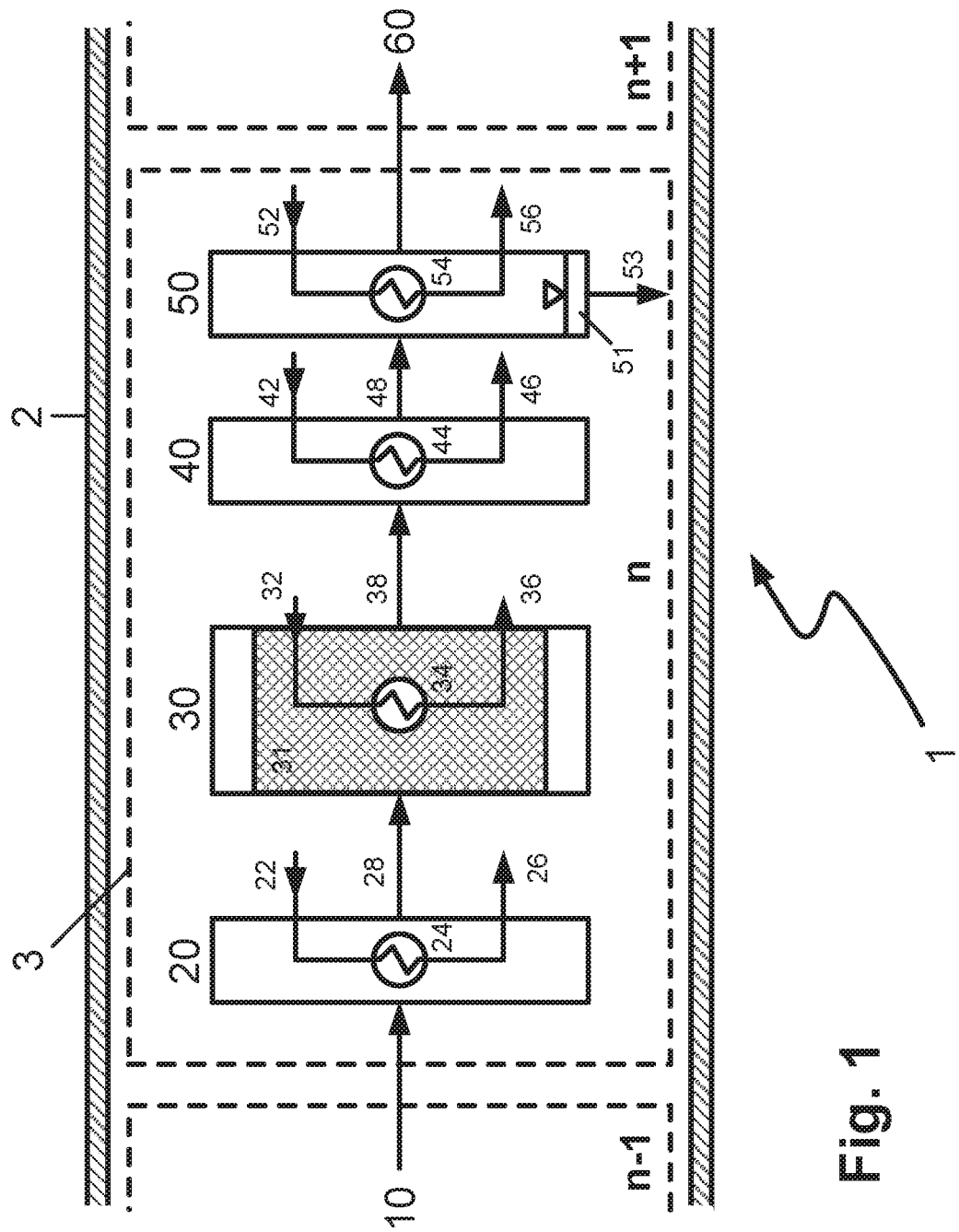

dinate of the reactor. For this purpose, in the process according to the invention, a reactor is used which is divided into a multitude of series-connected reaction cells, each of which comprises a preheating zone, a cooled reaction zone, one or more cooling zones and a deposition zone for condensable reaction products. In this way, the reaction conditions are adjustable to the respective, local composition of the reaction mixture and variable over the reactor length.

11 Claims, 7 Drawing Sheets

(51) Int. Cl.
*C07C 29/152* (2006.01)
*C07C 31/04* (2006.01)

(52) U.S. Cl.
CPC .............. *B01J 2208/0053* (2013.01); *B01J 2208/00176* (2013.01); *B01J 2219/0004* (2013.01); *C07C 31/04* (2013.01)

(58) Field of Classification Search
CPC ...... B01J 8/0446; B01J 8/0449; B01J 8/0457; B01J 8/0496; B01J 19/00; B01J 19/24; B01J 2208/00; B01J 2208/00008; B01J 2208/00017; B01J 2208/00106; B01J 2208/00168; B01J 2208/00176; B01J 2208/0053; B01J 2219/00; B01J 2219/00002; B01J 2219/00027; B01J 2219/0004; C07C 29/00; C07C 29/15; C07C 29/151; C07C 29/152; C07C 31/00; C07C 31/02; C07C 31/04
See application file for complete search history.

(56) References Cited

U.S. PATENT DOCUMENTS

| | | |
|---|---|---|
| 5,827,901 A | 10/1998 | Konig et al. |
| 7,683,099 B2 | 3/2010 | Hipp |
| 8,629,190 B2 | 1/2014 | Kopetsch |
| 10,364,202 B2 | 7/2019 | Kopetsch et al. |
| 2010/0280136 A1 | 11/2010 | Tonkovich et al. |
| 2016/0159714 A1 | 6/2016 | Zubrin et al. |

FOREIGN PATENT DOCUMENTS

| | | | |
|---|---|---|---|
| DE | 2 934 332 | 3/1981 | |
| DE | 10 2008 049622 | 4/2010 | |
| EP | 0 483 919 | 5/1992 | |
| EP | 0 494 350 | 7/1992 | |
| EP | 0 682 002 | 11/1995 | |
| EP | 0 790 226 | 8/1997 | |
| EP | 1 016 643 | 7/2000 | |
| EP | 3 219 697 | 9/2017 | |
| WO | WO 01/17936 | 3/2001 | |
| WO | WO 2005/115607 | 12/2005 | |
| WO | WO 2007/096699 | 8/2007 | |
| WO | WO 2012/139703 | 10/2012 | |
| WO | WO 2015/030578 | 3/2015 | |
| WO | WO 2015/193440 | 12/2015 | |
| WO | WO-2017157530 A1 * | 9/2017 | ............. C01B 3/501 |

OTHER PUBLICATIONS

International Search Report and Written Report for PCT/EP2018/025131, dated Jun. 26, 2018.
International Search Report and Written Opinion for PCT/EP2018/025129, dated Jul. 3, 2018.

* cited by examiner

PROCESS FOR CONDUCTING EXOTHERMIC EQUILIBRIUM REACTIONS

CROSS REFERENCE TO RELATED APPLICATIONS

This application is a § 371 of International PCT Application PCT/EP2018/025131, now WO2018/206155, filed Apr. 26, 2018, which claims the benefit of EP17400025.7, filed May 12, 2017, both of which are herein incorporated by reference in their entireties.

FIELD OF THE INVENTION

The invention relates to a process for conducting exothermic equilibrium reactions, especially for the performance of methanol synthesis by heterogeneously catalysed conversion of synthesis gas comprising hydrogen and carbon oxides over solid catalysts.

BACKGROUND OF THE INVENTION

Processes for performance of exothermic equilibrium reactions have long been known in the field. A reaction of this type which is of particular industrial importance is methanol synthesis by heterogeneously catalysed conversion of synthesis gas, i.e. mixtures of hydrogen and carbon oxides. Ullmann's Encyclopedia of Industrial Chemistry, Sixth Edition, 1998 Electronic Release, "Methanol" chapter, sub-chapter 5.2 "Synthesis", describes various basic processes for preparing methanol by catalytic conversion of synthesis gas comprising hydrogen and carbon oxides, in which such reactors are used.

A modern, two-stage process for preparing methanol is known, for example, from European patent specification EP 0 790 226 B1. The methanol is prepared in a cycle process in which a mixture of fresh and partly reacted synthesis gas is first fed to a water-cooled reactor and then to a gas-cooled reactor, in which the synthesis gas is converted in each case to methanol over a copper-based catalyst. The methanol prepared in the process is separated out of the synthesis gas to be recycled, which is then conducted through the gas-cooled reactor in countercurrent as coolant and is preheated to a temperature of 220 to 280° C., before it is introduced into the first synthesis reactor. A portion of the synthesis gas to be recycled is removed from the process as purge stream in order to prevent inert components from accumulating within the synthesis circuit. This measure is also taught in German published specification DE 2934332 A1 and European patent application EP 1016643 A1.

The main conversion of the synthesis gas ($CO$, $CO_2$, $H_2$) is typically achieved in the water-cooled reactor stage, and the majority of the heat of reaction is removed, while a nevertheless considerable proportion of the synthesis gas is converted under milder conditions in the gas-cooled stage.

In some plant configurations, an intermediate condensation stage is additionally provided between the two reaction stages, in order to reduce the proportion of reaction products formed (predominantly methanol and water) in the feed gas to the second reaction stage and hence to further increase the achievable conversion of the reactants. A plant configuration of this kind is taught, for example, in German patent specification DE 10 2008 049 622 B4.

The water-cooled reactor (WCR) is typically a tubular reactor having corresponding tube plates, in which the catalyst is introduced into the tubes, while the cooling is effected by means of boiling water or steam generation on the shell side around the tubes. In the gas-cooled reactor (GCR), the cooling is effected with the feed gas which is guided through the tubes and is heated on its way to the first reaction stage (WCR), while the catalyst is introduced around the tubes and the reaction takes place on the shell side of the GCR. In terms of their nominal width, the reaction stages are connected to large or very large pipelines; according to plant capacity, pipe diameters of up to 1 m are possible. This is particularly because of the large volumes of gas that are recycled to the second stage (recycle gas) and are mixed with the fresh gas, i.e. fresh synthesis gas from the gas production. The resulting gas mixture of recycle gas and fresh gas, after being preheated in the GCR, is fed to the first reaction stage (WCR). The volume of recycle gas is typically much greater than the amount of fresh gas and is dependent on the conversion achieved in the reactor section. The recycle ratio RR ($RR=R/F$) of recycle gas volume (R) to fresh gas volume (F) is often above 2 and in some cases is even above 3.5. The lower the conversion of synthesis gas through the reactor section per pass, the higher the recycle ratio RR required to achieve an adequate yield.

This correspondingly increases the circulating gas volume, which increases the stress on the reactors and requires greater nominal pipe widths of the connecting pipelines and also leads to a higher demand for compression energy (higher flow rate and pressure drop).

SUMMARY OF THE INVENTION

The problem addressed by certain embodiments of the present invention is therefore that of specifying a process which does not have the described disadvantages of the processes known from the prior art and which especially gives a high conversion based on the target products of the exothermic reaction and the option of readjusting and hence optimizing the reaction conditions along the longitudinal coordinate of the reactor, which in the case of the methanol synthesis, for example, leads to a reduction in the recycle ratio to smaller values as known in the case of use of the processes known from the prior art.

This problem is solved by a process having the features of certain embodiments of the invention described herein.

Inventive Process:

Process for preparing methanol by converting a synthesis gas feed comprising hydrogen and carbon oxides, comprising the following process steps:

(a) providing a reactor comprising the following series-connected assemblies that are in fluid connection with one another:

(aa) a preheating zone suitable for heating the feed mixture or the gaseous product stream from the upstream reaction cell, wherein the preheating zone can optionally be dispensed with in the first reaction cell in flow direction of the gaseous feed mixture, (ab) at least one reaction zone comprising a catalyst active in respect of the exothermic equilibrium reaction to be conducted and a cooling apparatus in a heat-exchanging relationship with the catalyst, (ac) at least one cooling zone comprising a cooling apparatus suitable for cooling the partly converted, gaseous product stream that has been laden with condensable reaction product and exits from the reaction zone to a temperature below the dew point of this gas, (ad) a deposition zone comprising a phase separation apparatus for separation of the product stream that exits from the cooling zone into a gaseous product stream that has been freed of condensate and a condensate stream comprising liquid reaction product, (ae) means of discharging the condensate stream comprising liquid reaction product and optionally means of feeding the condensate stream to a workup apparatus for the reaction product, (af) means of discharging the gaseous product stream that has been freed of condensate and means of feeding this gaseous product stream to a subsequent reaction cell arranged downstream or means of discharging the gaseous product stream from the process, (b) providing a synthesis gas feed comprising hydrogen and carbon oxides and introducing it into the reactor, (c) at least partly converting the synthesis gas feed in the reactor under methanol conversion conditions, (d) discharging a liquid reactor product stream comprising methanol and water from the reactor and optionally feeding the liquid reactor product stream to a further deposition apparatus and/or at least one further methanol workup apparatus, (e) discharging a synthesis gas output stream and recycling this synthesis gas output stream to the reactor with a fixed recycle ratio and/or discharging the synthesis gas output stream from the process.

Fluid connection between two regions of the reactor of the invention is understood to mean any kind of connection that enables flow of a fluid, for example the feed gas stream or the synthesis gas product stream, from one to the other of the two regions, regardless of any intermediately connected regions or components.

What is meant by a heat-exchanging relationship is the possibility of heat exchange or heat transfer between two regions of the reactor according to the invention, wherein all mechanisms of heat exchange or heat transfer, such as conduction of heat, radiation of heat or convective heat transfer, may be manifested. An indirect heat-exchanging relationship is especially understood to mean the manner of heat exchange or of heat transfer through a wall (called passage of heat), which comprises the stages of heat transfer from fluid 1 to the surface of the wall, of conduction of heat through the wall and of heat transfer from the surface of the wall to fluid 2.

Methanol conversion conditions are understood to mean the process conditions that are known per se to the person skilled in the art, especially of temperature, pressure and residence time, as mentioned above by way of example and discussed in detail in the relevant literature, and under which there is at least partial conversion, but preferably conversions of industrial relevance, of the CO or $CO_2$ and hydrogen reactants to the methanol product. Correspondingly, a catalyst active in respect of the methanol synthesis is understood to mean a catalyst which brings about exactly such conversions under methanol conversion conditions.

Means of introduction, discharge, etc. are understood to mean all the apparatuses, apparatus constituents, assemblies and components which enable the fluid in question to leave the spatial region in question, for example a vessel. This is especially understood to mean pipelines, pumps, compressors, other conveying devices and the corresponding passage orifices in the vessel wall.

The catalytic activity, especially in connection with a different catalytic activity on comparison of two different catalysts, is understood to mean the degree of conversion achieved per unit length of the catalyst bed from reactants to products. The activity is affected by the chemical composition, doping, poisoning, available surface area etc. of the catalyst material, but also by the geometry of the catalyst particles and textural parameters of the catalyst bed, for example the porosity or packing density thereof. Owing to the exothermicity of the reactions in question, a high catalytic activity correlates with a high release of heat per unit length of the catalyst bed.

The option mentioned in claim 1. (aa) that the preheating zone in the first reaction cell in flow direction of the gaseous feed mixture can be dispensed with is implemented especially when a heating apparatus arranged outside the reactor according to the invention and connected upstream thereof is present, which assures the setting of the reaction temperature prior to entry into the first reaction zone.

The invention is based on the finding that an optimal temperature regime and repeated removal of products from the reaction zone can distinctly improve the production rates or space-time yields along the reaction pathway. The temperature profile along the reaction pathway is considerably improved by the use of a multistage reaction system, which achieves a distinctly higher conversion per pass.

By-product formation in the methanol synthesis is also reduced when the process according to the invention is performed compared to the prior art.

An improved temperature profile in the reactor can in principle also be achieved with the aid of catalyst layer management. In this case, a less active catalyst would be used in the region in which the highest conversion (exothermicity) and hence the highest temperatures would be expected, and a more active catalyst in regions where less conversion is expected. However, such catalyst layer management is relatively inflexible since the various catalyst layers have to be selected and fixed on the basis of a particular catalyst activity and a corresponding gas composition. However, the catalyst activity changes as a result of its progressive deactivation over its onstream time in the synthesis plant.

The layer management and the corresponding cooling of the reaction bed have to be matched to one another. During the catalyst onstream time and the associated catalyst deactivation, the conditions change, and adjustment of the reaction temperature and the corresponding cooling/cooling temperature is desirable in order to at least partly compensate for the deactivation and to ensure a high conversion with low by-product formation. With the reactors known from the prior art, adjustment of the cooling can be undertaken for the entire reactor only; but not all catalyst layers are typically deactivated to the same degree over the operating time. The establishment of specific reaction conditions is therefore always a compromise.

By the approach according to the invention, the reaction conditions in the different reaction cells, by contrast, can also be adapted individually over the onstream time in each stage depending on the catalyst activity, the gas composition. In this way, a high conversion and low by-product formation are achieved in the various reaction cells.

With the optimized temperature regime, the maximum temperatures (and temperature peaks, called hotspots) in the catalyst bed are also reduced. As well as the discharge of the coproduct from the reaction system, for example of water in the methanol synthesis, this has a positive effect on the catalyst onstream time. It is known that both high temperatures in the catalyst bed and high water concentrations in the reaction gas lead to more rapid catalyst deactivation.

With the concept proposed, an improved space-time yield is achieved; it is thus also possible to considerably reduce the recycle gas volume (gas circulation). In principle, the reactor can thus be reduced in size and the pressure drop can also be reduced. Another result of the reduction in the recycle gas volume is that the amount and concentration of accumulated inert gases, for example unconverted methane from the synthesis gas production, in the synthesis gas circuit are distinctly reduced and hence the burden on the entire methanol synthesis cycle comprising reactor stages, circulation compressors and further equipment is reduced. The optimum can be considered to be the full conversion per reactor pass, where it would be possible to entirely dispense with a synthesis gas circuit and, therefore, no accumulation of inert gases occurs any longer. Such an approach is also of particular interest for other feed gas compositions with high inert gas components (for example a high proportion of nitrogen in synthesis gas production using air), since there is a rise in the volume of inert gas to be circulated in the synthesis gas circuit.

By controlled deposition of the liquid products and temperature control in the individual reaction cells, condensation in the catalyst bed is avoided and the catalyst is spared.

The condensates separated out with different proportions of methanol can be purified under different conditions or used directly as feed for downstream processes, which leads to an energy saving in the distillation.

In order to keep the apparatus complexity and the capital costs low, in accordance with the invention, multiple reaction stages or reaction cells and also multiple intermediate condensations and cooling and heating stages are implemented in one reactor. Connecting pipelines are avoided as far as possible, so as to reduce capital costs for pipelines and the pressure drop and to decrease the stress on the pipelines resulting from thermomechanical stresses. The process media are as far as possible guided from process stage to process stage within the apparatus.

A particular configuration of the process according to the invention is characterized in that the recycle ratio is zero. The reduction in the cycle gas volume to zero results in a considerable reduction not just in the reactor size but also in the dimensions of the pipelines. Moreover, the circulation compressor which is customary in the processes for methanol synthesis known from the prior art is dispensed with, and there is a reduction in the compression energy required.

Another result of the considerable reduction in the volume of recycle gas, ideally down to zero, is that the amount and concentration of accumulated inert gases, for example unconverted methane from the synthesis gas production, in the synthesis gas circuit is distinctly reduced, and hence the burden on the entire synthesis gas circuit comprising reactor stages, circulation compressors and further equipment is reduced. The optimum can be considered to be an almost complete conversion per reactor pass, in which it would be possible to dispense with circulation of gas and no accumulation of inert gases occurs any longer. Such an approach would also be of particular interest for feed gas mixtures having high proportions of inert gas (for example high nitrogen content in the case of synthesis gas production using air), since, in the presence of a gas circuit, the amount of inert gas to be circulated would rise significantly, which is a burden on the economic viability of the process.

A further advantageous configuration of the process according to the invention envisages that the amount of catalyst in the individual reaction zones (b) of the individual reaction cells decreases in flow direction of the synthesis gas through the reactor. Comparative tests and comparative calculations show that, under these conditions, the conversion of carbon oxides and the space-time yield in kg of methanol per litre of catalyst volume and per hour $kg_{MeOH}/(litre_{cat}\ h)$ are higher than in the case of a rising or equal amount of catalyst in the individual reaction zones of the individual reaction cells in flow direction of the synthesis gas.

A further aspect of the process according to the invention is characterized in that the temperature of the cooling medium in the reaction zones (b) of the individual reaction cells is between 180 and 300° C., preferably between 190 and 270° C., most preferably between 200 and 260° C., and remains the same or decreases in flow direction of the synthesis gas through the reactor. Comparative tests and comparative calculations show that, under these conditions, the conversion of carbon oxides and the space-time yield in kg of methanol per litre of catalyst and per hour $kg_{MeOH}/(litre_{cat}\ h)$ are higher than in the case of a rising temperature of the cooling medium in the individual reaction zones of the individual reaction cells in flow direction of the synthesis gas. The temperature of the cooling medium remaining the same is understood to mean a change in temperature of not more than 5 K.

It is particularly preferable when, in the process according to the invention, the condensation temperature in the cooling zones of the individual reaction cells is between 20 and 120° C., preferably between 40 and 100° C., and remains the same or decreases in flow direction of the synthesis gas through the reactor. Comparative tests and comparative calculations show that, under these conditions, the conversion of carbon oxides and the space-time yield in kg of methanol per litre of catalyst and per hour $kg_{MeOH}/(litre_{cat}\ h)$ are higher than in the case of a rising condensation temperature in flow direction of the synthesis gas.

In a further aspect of the process according to the invention, the same heat carrier is used in all reaction cells and the temperature employed is the respective boiling point at different pressure levels and corresponding vapour temperatures. This gives rise to logistical and technical advantages since just a single heat carrier has to be held in stock, and circuits for the supply and removal of further heat carriers are dispensed with.

In a further aspect of the process according to the invention, all reaction cells are connected to the same steam generator and the heat carrier is provided in liquid form and undergoes at least partial evaporation in the region of the reaction cells. Advantages arise here too, since just a single steam generator has to be provided. Since a particularly large change in enthalpy is associated with the evaporation, the heat of reaction released in the reaction cells can be removed particularly effectively in this way.

Heat carriers used are preferably heat carrier oil or water. Both heat carriers are easy to handle and obtainable easily and inexpensively.

BRIEF DESCRIPTION OF THE INVENTION

Developments, advantages and possible uses of the invention will also be apparent from the description of working examples which follows and the drawings. The invention is formed by all the features described and/or shown in figures, alone or in any combination, irrespective of their assembly in the claims or the dependency references thereof.

Figure 2:
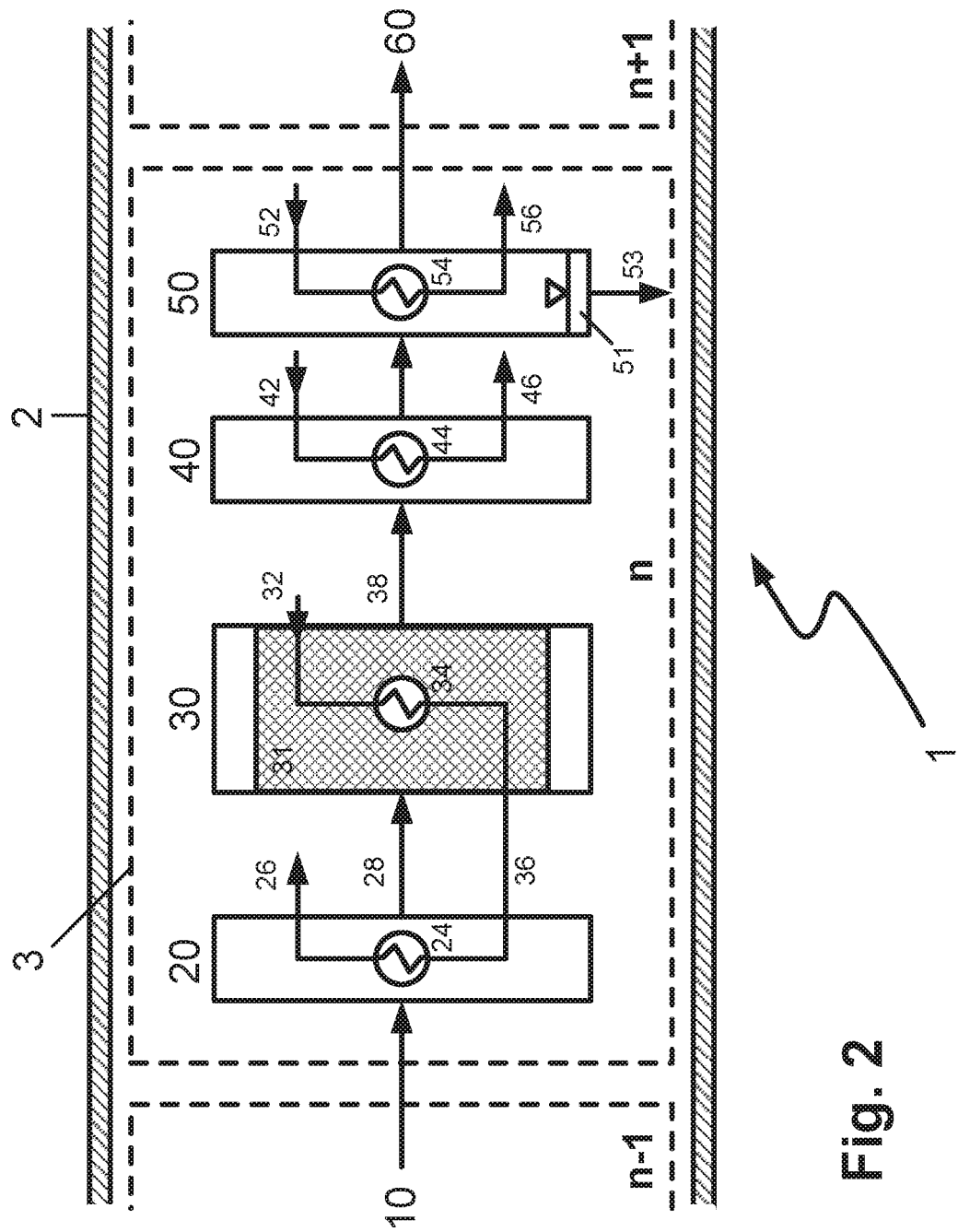
Figure 3:
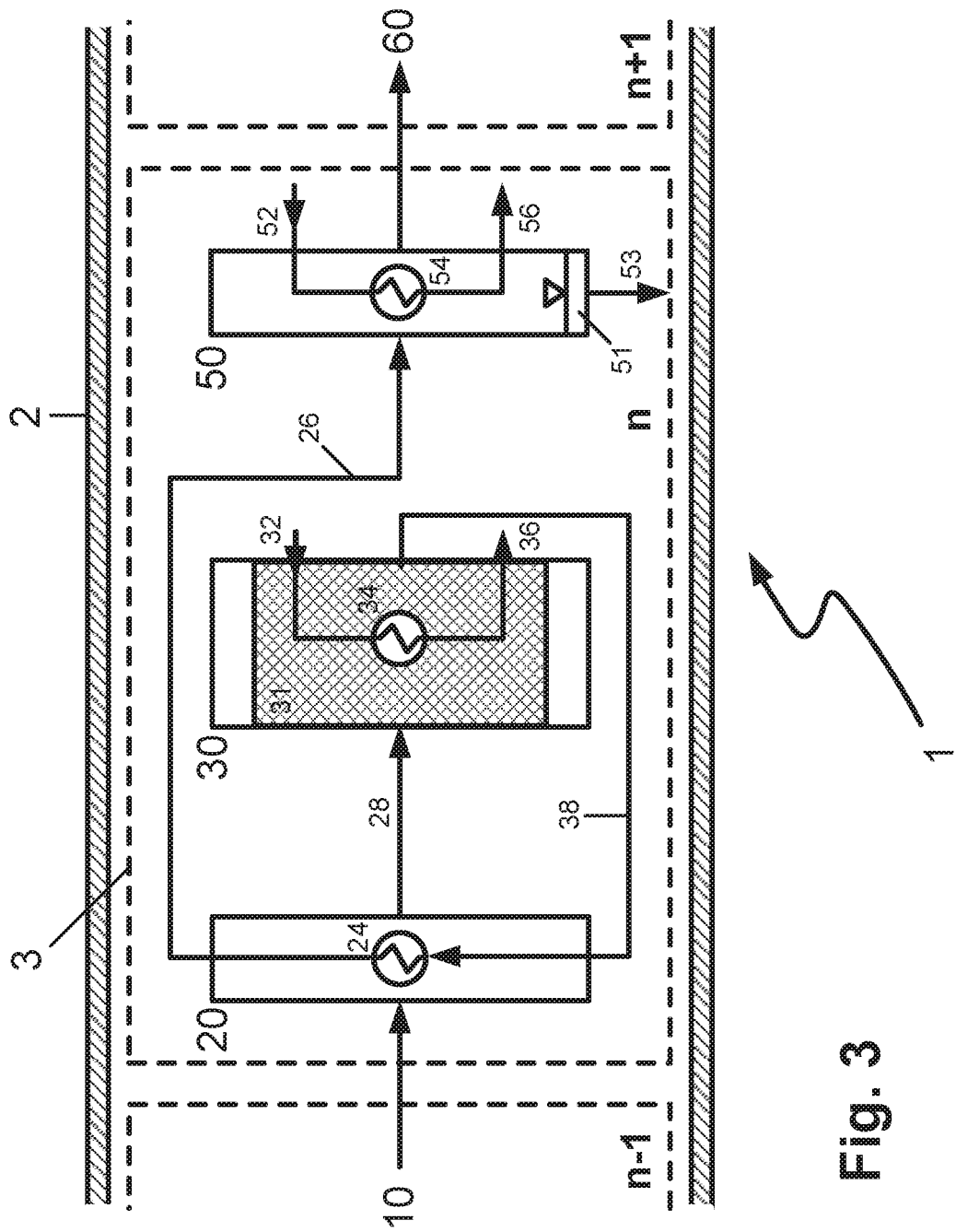
Figure 4:
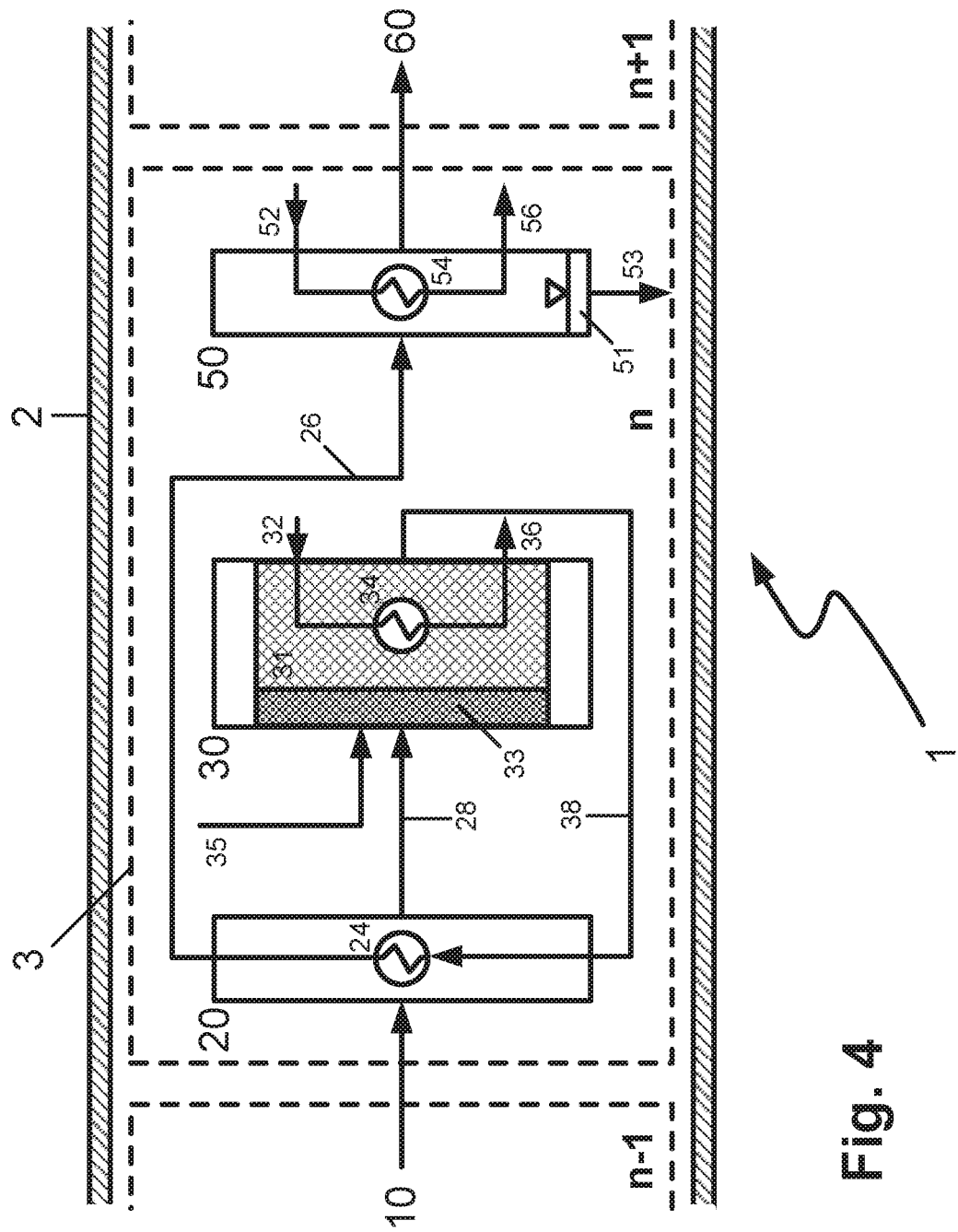
Figure 5:
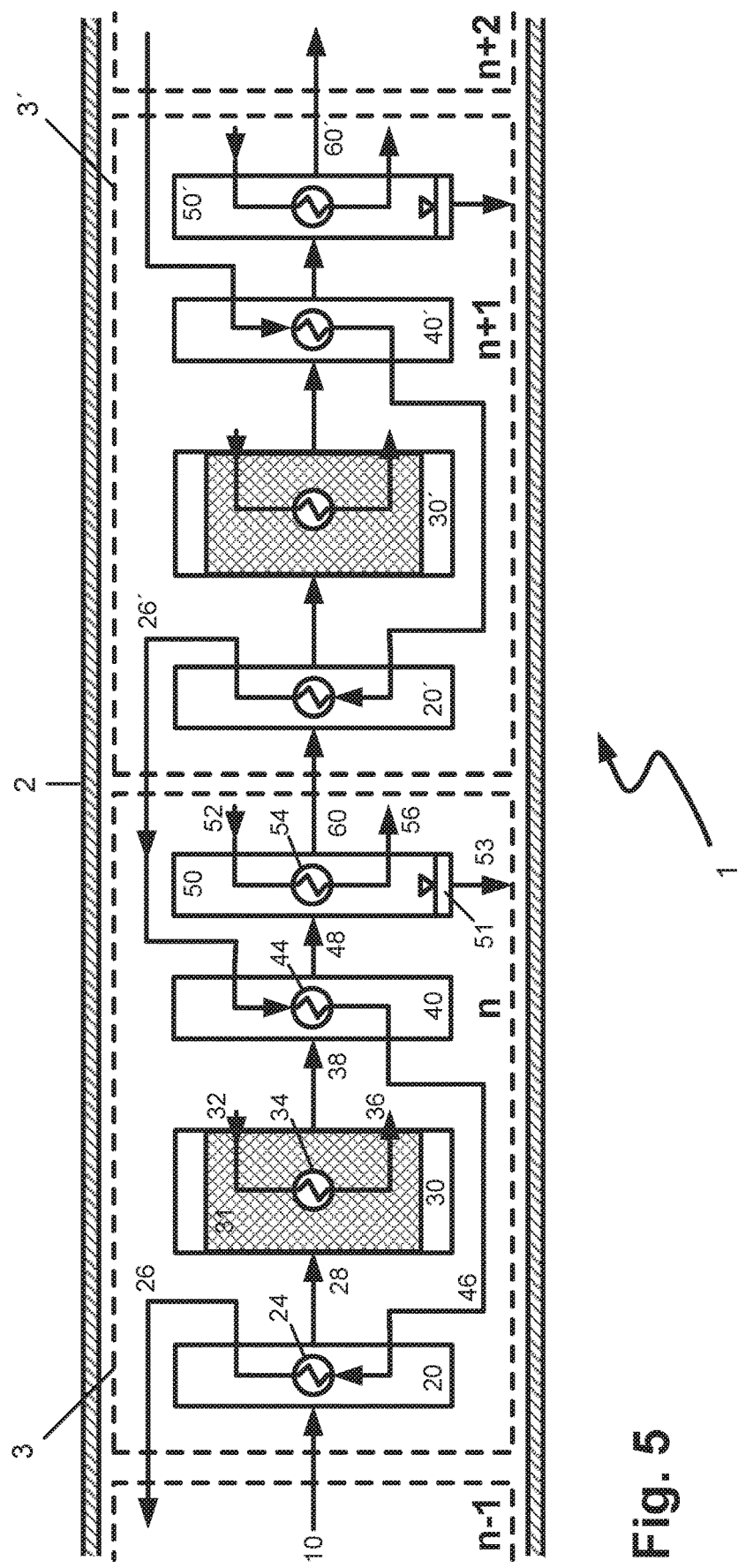
Figure 6:
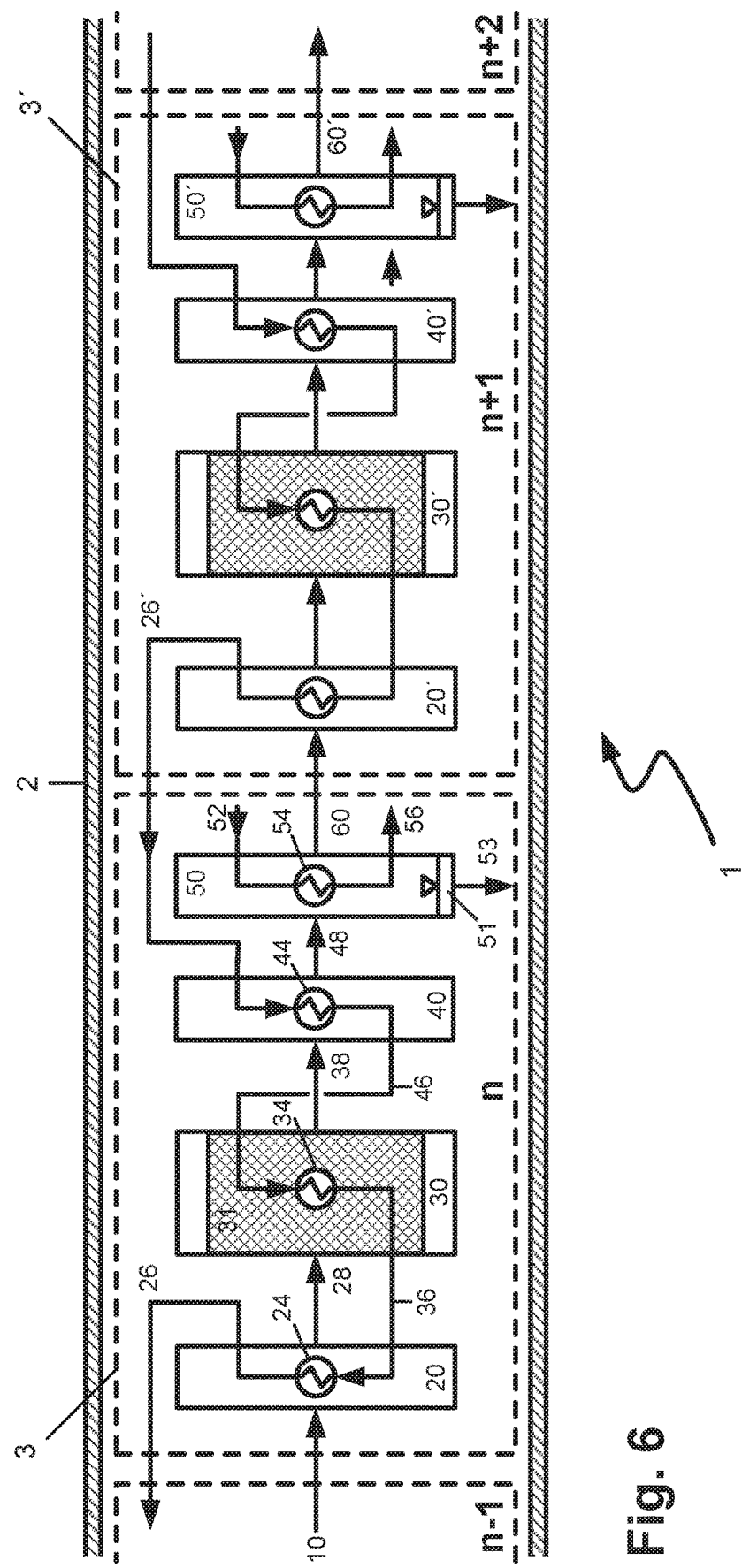
Figure 7:
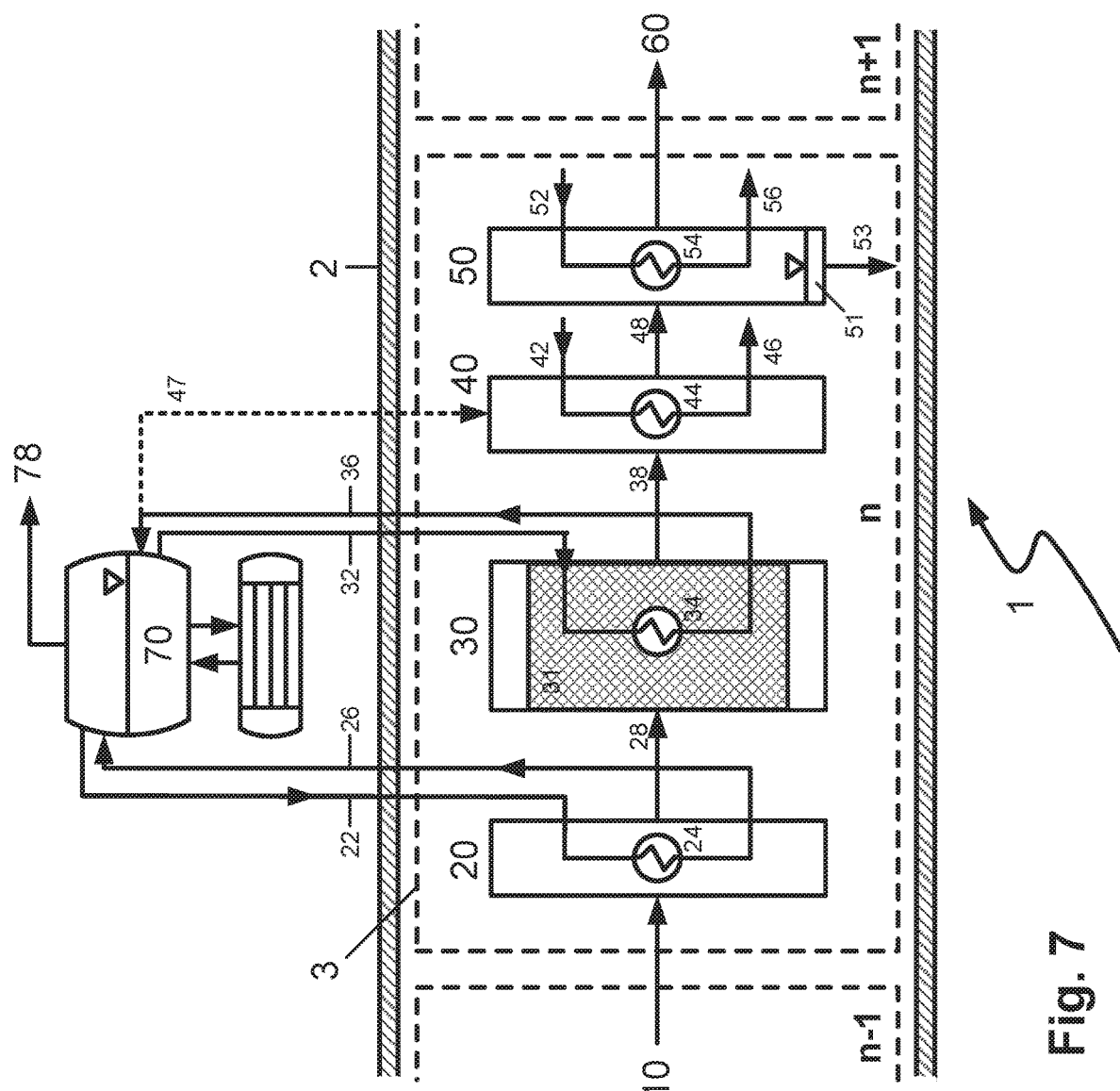

The figures show:

FIG. 1 a reaction cell in a reactor in a first embodiment of the invention,

FIG. 2 a reaction cell in a reactor in a second embodiment of the invention,

FIG. 3 a reaction cell in a reactor in a third embodiment of the invention,

FIG. 4 a reaction cell in a reactor in a fourth embodiment of the invention,

FIG. 5 a first example of the connection of two successive reaction cells in a reactor according to the invention, FIG. 6 a second example of the connection of two successive reaction cells in a reactor according to the invention, FIG. 7 a working example for the connection of a reaction cell in a reactor according to the invention having a steam generator.

DETAILED DESCRIPTION OF THE INVENTION

FIG. 1 is a schematic diagram of a reaction cell 3 in a reactor 1 in a first embodiment of the invention. The reaction cell n is within the reactor shell 2, the inner wall of which forms the outward physical boundary of the reactor and bears the pressure chosen for the performance of the exothermic equilibrium reaction.

Via conduit 10, the preheating zone 20 is supplied, in the reaction cell n, with the gaseous, prereacted product stream from the preceding reaction cell n−1 arranged upstream. If the reaction cell n is the first reaction cell in flow direction, the feed mixture is fed in via conduit 10.

In the preheating zone 20, the gaseous product stream or the feed mixture is heated up to the reaction temperature. This is effected in indirect heat exchange against a heating fluid which is fed via conduit 22 to the heat exchanger 24, where it transfers its heat content to the gaseous product stream or the feed mixture. The cooled heating fluid is removed from the heat exchanger via conduit 26 and heated up in a heating apparatus which is not shown in the figure, in order to feed it back to the heat exchanger 24.

The heated feed mixture or the heated gaseous product stream is fed via conduit 28 to the reaction zone 30 which contains a bed of a catalyst 31 active in respect of the exothermic equilibrium reaction to be performed and a cooling apparatus 34 in a heat-exchanging relationship with the catalyst. The heat of reaction released by the exothermic reaction is removed in indirect heat exchange against a cooling fluid, optionally in partly evaporated form, which is fed via conduit 32 to the heat exchanger 34 and, after absorbing the heat of reaction released in the catalyst bed, is removed via conduit 36. The heated cooling fluid is cooled down again in a cooling apparatus which is not shown in the figure, in order to feed it back to the heat exchanger 34.

In the reaction zone, under the reaction conditions chosen, the feed mixture or the gaseous product stream from the reaction cell n−1 is partly converted in the catalyst bed to a gaseous product stream laden with condensable reaction product, which is removed from the reaction zone via conduit 38 and fed to a first cooling zone 40.

In the first cooling zone 40, the gaseous product stream laden with condensable reaction product is subjected to preliminary cooling, wherein the first proportions of condensate can already be obtained, which can be discharged from the reactor 1 via a deposition apparatus, not shown in the figure, and conduits. Alternatively, the preliminary cooling can also be conducted in the first cooling zone in such a way that the temperature does not yet go below the dew point of the gas stream. The preliminary cooling is effected in indirect heat exchange against a cooling fluid which is fed via conduit 42 to the heat exchanger 44 and, after absorbing heat, removed via conduit 46. The heated cooling fluid is cooled again in a cooling apparatus, not shown in the figure, in order to feed it back to the heat exchanger 44.

The gaseous product stream that has been precooled but is still laden with at least a portion of the condensable reaction product is discharged from the first cooling zone via conduit 48 and fed to the second cooling zone 50. In the second cooling zone 50, the gaseous product stream laden with condensable reaction product is cooled further, going below its dew point. This affords a liquid condensate which is separated from the gas stream by means of a deposition apparatus 51 integrated into the second cooling zone and discharged from the reactor by means of conduit 53 and fed to the product workup system which is not shown in the figure. The cooling is effected in indirect heat exchange against a cooling fluid which is fed via conduit 52 to the heat exchanger 54 and, after absorbing heat, removed via conduit 56. The heated cooling fluid is cooled down again in a cooling apparatus not shown in the figure, in order to feed it back to the heat exchanger 54.

The gaseous product stream that has been cooled and freed of condensate is discharged via conduit 60 from the second cooling zone 50 and hence also from the reaction cell n. It is then fed to the downstream reaction cell n+1 in order to enable further conversion of the gaseous reactants to target products. If no further conversion of the gaseous reactants is desirable or possible, the remaining tail gas is discharged from the reactor via conduit 60 and sent for further workup or disposal. Alternatively, the tail gas stream can be applied to the reactor again after recycling and mixing with fresh feed mixture.

In the configurations shown in schematic form in FIG. 2 to FIG. 7, identical reference numerals correspond in principle to the apparatus constituents as already described in the elucidation of the first configuration of the invention, FIG. 1. The respective operating steps and process conditions are also the same, unless described differently hereinafter.

By contrast with the first configuration, in FIG. 2, the cooling fluid heated up by absorption of the heat of reaction in the reaction zone 30 is conducted via conduit 36 to the heat exchanger 24 of the preheating zone 20, where it is used as heating fluid for the heating of the feed mixture or the gaseous product stream from the upstream reaction cell. In this way, thermal integration within the reactor is improved. This option is of particular interest when a (partly) evaporating cooling medium is used in the reaction zone 30 and is at least partly condensed again in the preheating zone 20, where it is used as heating medium. In the case of a vertical arrangement of preheating zone (at the top) with a reaction zone beneath, this can be achieved in a simple manner with a single arrangement comprising an upper preheating zone without catalyst and a lower reaction zone comprising catalyst, which are directly connected on the heat exchanger side. Steam formed from the reaction zone ascends and is used at least partly as heating medium in the preheating zone; condensed steam flows back to the reaction zone in liquid form. The heating fluid cooled down by heat exchange with the gas stream supplied in conduit 10 can subsequently, optionally after further cooling in a cooling apparatus not shown in the figure, be recycled as cooling fluid via conduit 32 to the heat exchanger 34 of the reaction zone 30.

By contrast with the first configuration, in FIG. 3, the product stream discharged from the reaction zone 30 via conduit 38 is guided as heating fluid to the heat exchanger 24 of the preheating zone 20, where it serves to heat up the feed mixture or gaseous product stream brought in via conduit 10 from the upstream reaction cell. The preheating zone 20 and the first cooling zone 40 thus coincide. In this way too, thermal integration within the reactor is improved.

The product stream cooled by heat exchange is then guided via conduit 26 to the second cooling zone 50.

By contrast with the above-elucidated configuration according to FIG. 3, the reaction zone in FIG. 4 contains two beds of catalysts 31, 33 having different activity in respect of the exothermic equilibrium reaction, through which the feed mixture or gaseous product stream from the upstream reaction cell flows successively. In the configuration shown, only the downstream catalyst bed 31 is cooled by means of the cooling apparatus 34. One possible configuration envisages that the catalyst bed 33 contains a catalyst having a higher activity compared to the catalyst bed 31. In this way, the catalytic conversion can first be set in motion and the amount of heat released contributes to the heating of the reaction mixture to the chosen inlet temperature into the catalyst bed 31, which means that the heat exchanger 24 in the preheating zone 20 can be reduced in size. For this function as ignition catalyst, experience has shown that a small or short catalyst bed in relation to the main catalyst bed 31 is sufficient. The reaction in the main catalyst bed 31 then proceeds more homogeneously, since spikes in concentration of the reactants are already reduced in the catalyst bed 33 and, in addition, the catalyst bed 31 is cooled. This avoids the formation of hotspots.

Alternatively, it is possible to use a catalyst having lower activity compared to the catalyst bed 31 in the catalyst bed 33. This is advisable particularly when the reaction potential of the gas mixture that occurs in the reaction zone is high. This is the case in the configuration shown in FIG. 4 since, via conduit 35, the reaction zone 30 is supplied in the reaction cell n with fresh, i.e. as yet non-prereacted feed mixture. In this way, the reaction is set in motion in a slower and more controlled manner and the majority of the heat of reaction is released in the cooled catalyst bed 31.

The feeding of fresh, as yet non-prereacted feed mixture to reaction cells with n>1 may also be viable in conjunction with the other configurations of the reactor according to the invention that have been discussed here. In addition, it may be advantageous to feed fresh, as yet non-prereacted feed mixture to more than one reaction cell with n>1.

The configuration shown in schematic form in FIG. 5 shows one possible connection of two successive reaction cells n and n+1. Corresponding apparatus constituents of the reaction cell n+1 are identified by an apostrophe ' after the respective reference numeral. In this case, cooled heating fluid from the preheating zone 20' of the reaction cell n+1 is fed via conduit 26' to the heat exchanger 44 in the first cooling zone 40 of the reaction cell n, where it serves to precool the gas stream removed from the reaction zone 30 via conduit 38. Correspondingly, cooled heating fluid from the preheating zone 20 from the reaction cell n is fed via conduit 26 to the corresponding heat exchanger in the first cooling zone of the reaction cell n−1. In this way, even further thermal integration within the reactor is achieved, which now extends over multiple reaction cells. The heating fluid heated up in the heat exchanger 44 is fed via conduit 46 to the heat exchanger 24, where it serves to preheat the mixture entering the reaction cell n via conduit 10.

By contrast with the above-discussed configuration according to FIG. 5, in the working example of FIG. 6, in addition, the heated coolant removed from the respective first cooling zone 40, 40' etc. is fed to the heat exchanger of the respective upstream reaction zone 30, 30' etc. as coolant. The coolant which is heated further in the reaction zone is subsequently fed to the heat exchanger of the respective upstream preheating zone as heating fluid. This configuration may especially be suitable for conducting moderately exothermic reactions. It is still favourable in the context of this configuration to use a cooling fluid/heating fluid having high heat absorption and heat release capacity; suitable fluids for this purpose are especially those which, when used as cooling fluid or heating fluid, have a liquid-vaporous phase transition or vice versa. Finally, it can be advisable to cool the reaction zones by means of further cooling apparatuses not shown in the figure in order to have a more intense cooling effect and more degrees of freedom with regard to the temperature regime in the reaction zone.

In the last two configurations discussed, it may additionally be advisable to feed the heated cooling fluids or cooled heating fluids first to one or more cooling or heating apparatuses arranged outside the reactor, in order to restore the full heat absorption or heat release capacity of the respective fluid. These external cooling or heating apparatuses could be arranged, for example, within the flow pathway of the conduits 26, 26' etc. (heating), 46, 46' etc. (cooling) or 36, 36' etc. (cooling).

The connection with an external cooling or heating apparatus is shown in schematic form in the configuration shown in FIG. 7, in which a steam generator 70 is arranged outside the reactor. Hot condensate is withdrawn therefrom and fed as coolant via conduit 32 to the heat exchanger 34 of the reaction zone 30, where it is partly evaporated. The resulting biphasic mixture in liquid/vaporous form is recycled to the steam generator via conduit 36.

The hot condensate from the steam generator 70 can also be used as coolant in the first cooling zone 40; this is shown in schematic form by the dotted conduit 47.

Also withdrawn from the steam generator 70 is saturated steam, which is fed via conduit 22 to the heat exchanger 24 of the preheating zone 20. The release of heat to the stream brought in via conduit 10 results at least in partial condensation. The resulting stream can either be recycled directly via conduit 26 to the steam generator or can be collected by means of other apparatuses (not shown in the figure) and then at least partly recycled back to the steam generator, in order to be evaporated again there.

In the working example of FIG. 7, moreover, saturated steam can be removed from the steam generator 70 via a conduit 78 and released as export steam to external consumers.

The heat carriers or cooling media used are preferably media that are close to their boiling point and therefore readily evaporate (cooling medium) or condense (heat carrier, heating medium). This assures good removal of heat by virtue of good heat transfer on the part of the evaporating or condensing medium, and allows precise regulation of temperature via the pressure. In order to establish different temperature conditions in the various stages, the pressure is regulated individually for each stage on the part of the heat carrier or cooling medium. With increasing catalyst onstream time, the conditions are adjusted by means of appropriate setting of the pressure on the cooling medium side, and hence the reaction temperature is readjusted in order to keep the conversion correspondingly high.

With regard to the reaction conditions desired, it is possible for example to use steam as heat carrier in methanol synthesis. However, it is found that, when water is used, relatively large pressure differences have to be established for the desired temperature range in order to cover a broad temperature range (e.g. 250° C.: about 40 bar, 264° C.: about 50 bar). If, by contrast, an evaporating heat carrier oil (e.g. Dowtherm A) is used in a circuit for steam generation, it is possible to work within a very narrow pressure range and nevertheless to cover a large temperature range (e.g.: 255°

C.: 0.97 bar, 305° C.: 2.60 bar, corresponding to a temperature range of 50° C. with a pressure differential of just 1.6 bar. In this way, it is possible to work with a simple heat carrier oil/steam drum at the appropriate plant level (about 20 to 25 m), and to make use of the difference in height alone in order to establish the individual pressure or temperature ranges.

Cooling water or else an evaporating heat carrier can be used in the cooling zones and/or condensation zones, while a condensing or else liquid heat carrier can be used in the heating zones.

In many configurations, for example in all the configurations discussed above, it may be advantageous to form each of the heat transport spaces by means of at least one thermoplate. The heat transport spaces are understood to mean the regions of the reactor in which there is heat exchange between the gas flow containing the reactants or reaction products and heating or cooling fluids, i.e. the preheating zone, the reaction zone and the cooling zones.

A thermoplate in the context of the invention consists of two sheets which are bonded, preferably welded together, at the edges, and which have a multitude of additional bonds, preferably point welds, which likewise connect the plates to one another, distributed over the surface thereof. Plates of this kind can be manufactured in an automated manner by robots or machines and hence at very favourable cost. After the welding, the sheets are expanded by hydraulic forming, generally the injecting of a liquid under high pressure, which gives rise to cushion-shaped channels between the sheets, through which a heating or cooling fluid can be passed. By means of the heat transport spaces, therefore, heat energy can be either supplied to or removed from particular regions of the reactor through the passage of heating or cooling fluids.

When thermoplates are used, the reaction zones can be configured such that two thermoplates are first arranged essentially parallel in the reactor. "Essentially parallel" in the context of the invention means that the relative alignment of the thermoplates differs from parallel by a maximum of +/−20°, preferably by a maximum of +/−10°, more preferably by a maximum of +/−5°, most preferably by a maximum of +/−2°. Accordingly, the clear space between the thermoplates can be filled up with a bed of a solid, granular, particulate or pelletized catalyst, in which case the lateral closure of the resulting catalyst bed is formed by meshes, grids, perforated plates, grilles, beds of inert material and/or the inner reactor wall.

More preferably, this arrangement is adjoined by at least one, preferably more than one, further thermoplate spaced apart in a parallel arrangement, resulting overall in an assembly of plates, where the clear spaces between the thermoplates are filled up with catalyst beds. In this way, a compact, sandwich-like structure with an intensive cooling apparatus that extends over the length of the reaction zone is obtained in the reaction zone. The individual catalyst beds are charged here with the reaction gas mixture in parallel. The plate assemblies can, based on the clear spaces filled with catalyst, be aligned in parallel or at right angles to the longitudinal axis of the reactor.

The distances between the thermoplates are selected according to the exothermicity of the reaction to be conducted: for highly exothermic reactions, the distance chosen is smaller than for more weakly exothermic reactions. In this case, preference is given to smaller plate distances in the first reaction zone, since the greatest conversion is achieved here and the greatest removal of heat has to be implemented. The thermoplate distances in the first reaction zone, in the case of methanol synthesis, are preferably 20 to 45 mm. The distance is based on the distance from centre line to centre line, meaning that the clear distance between the plates, according to the thermoplate thickness and expansion of the cavity, is correspondingly smaller. Moreover, the distance is matched to the dimensions of the catalyst particles in order to assure optimal removal of heat and good bulk material characteristics in the filling and emptying of the catalyst without bridge formation. In the second and subsequent reaction zones, the distances chosen are typically greater.

Especially in the case of horizontal arrangement of the reactor with simultaneously vertical arrangement of the catalyst beds in the reaction zones, there is the possibility of simple removal of the catalyst from the reactor for the purpose of catalyst exchange. In this case, for emptying, appropriate inspection orifices should be provided in the reactor shell, which are actuated, for example, by means of a flap or slide mechanism. The slide mechanism can be executed in a very space-saving manner; it is advantageous here when the support grilles of the adjacent reaction zones can be moved one over the other by means of appropriate guide rails, such that adjacent regions can be emptied successively.

In a particular configuration, adiabatic, i.e. uncooled, reactor beds can be provided both downstream and upstream of the cooled plate assemblies. This may be of interest particularly when just a residual conversion is still to be achieved and cooling of the reaction is no longer necessary owing to the small evolution of heat, or on entry into a reaction stage where it is advantageous to achieve a rapid increase in temperature before the reactants enter the cooled region of the reaction zone.

In the case of the configuration of the preheating zone and cooling zones too, thermoplates can advantageously be used in the manner of a plate heat exchanger. It is possible here to dispense with the use of tube end plates as required in the case of shell-and-tube heat exchangers. Moreover, logistical and manufacturing advantages are obtained, since there is a reduction in the number of different components of the reactor and hence in the complexity of the apparatus.

A further possible configuration is enabled by the configuration of the heat transport spaces by means of lamellar heat exchangers (plate-fin heat exchanger) alternatively or additionally to the use of thermoplates.

Numerical Examples

Comparison with Reactors Known from the Prior Art

In the tables which follow, characteristic data for operation of the reactor in the process according to the invention are compared with reactors known from the prior art for the heterogeneously catalysed synthesis of methanol from synthesis gas.

In the first comparison case, a process according to the invention with a reactor having three reaction cells is compared with one with a three-stage industrial reactor comprising two water-cooled reactors WCR connected in parallel, followed downstream by a gas-cooled reactor GCR. The industrial plant does not have any intermediate condensation between WCR and GCR. The feed gas is the same in both cases in terms of its composition and flow rate; this is a synthesis gas having the following composition: 8.4% by volume of $CO_2$, 20.1% by volume of CO, 68% by volume of $H_2$, the remainder being inert components. The inlet pressure into the reactor in each case is 75 bar gauge. In Table 1, the essential comparative data for the two reactors are correlated. In the table, $X_{PP}(k)$ means the conversion of component k per pass through the reactor and $X_{tot}(k)$ the total conversion thereof over the reactor including gas circulation. STY is the space-time yield of methanol in kg/h, based on one litre of catalyst volume.

As apparent from the data collated in Table 1, the conversion of carbon oxides for the overall reactor is comparable in both cases; however, the conversions per reactor pass are much higher for the reactor according to the invention. For the latter, moreover, the maximum temperature in the catalyst bed, the concentration of by-products and the recycle ratio required are lower.

TABLE 1

Comparison of the characteristic data of the process according to the invention with a reactor having three reaction cells with a process with a three-stage methanol synthesis reactor (2 parallel WCRs + GCR) according to prior art.

| | Methanol synthesis reactor with 2 parallel WCRs + GCR Comparative Example | Reactor having three reaction cells Invention |
|---|---|---|
| $X_{pp}(CO)$/% | 81.9 | 95.5 |
| $X_{pp}(CO_2)$/% | 28.0 | 60.7 |
| $X_{pp}(CO_x)$/% | 54.6 | 82.7 |
| $X_{tot}(CO)$/% | 99.2 | 99.1 |
| $X_{tot}(CO_2)$/% | 85.4 | 84.4 |
| $X_{tot}(CO_x)$/% | 95.2 | 94.4 |
| STY(MeOH)/kg/(h litre$_{cat}$) | 0.86 | 1.26 |
| $V_{cat, tot}$/m$^3$ | 315 | 180 |
| $T_{in}$/° C. | 230 | 215 |
| $T_{max}$/° C. | 270 | 230 |
| By-products/ppm | 6200 | 3250 |
| Recycle ratio | 2.2 | 0.5 |

Table 2 below compares a process with a one-stage, water-cooled reactor for methanol synthesis with a process according to the invention with a reactor comprising four reaction cells, the process according to the invention being operated without recycling. The feed gas is the same in both cases with regard to composition and flow rate; this is a synthesis gas having the following composition: 7% by volume of $CO_2$, 16% by volume of CO, 73% by volume of $H_2$, the remainder being inert components. The inlet pressure into each of the reactors is 75 bar gauge.

TABLE 2

Comparison of the characteristic data of the process according to the invention with a reactor having four reaction cells without recycling with a process with a one-stage water-cooled methanol synthesis reactor

| | Methanol synthesis reactor (one-stage cooled reactor with high gas recycling rate) Comparative Example | Reactor having four reaction cells without gas recycling Invention |
|---|---|---|
| $X_{pp}(CO)$/% | 90.8 | 99.7 |
| $X_{pp}(CO_2)$/% | 62.8 | 93.9 |
| $X_{pp}(CO_x)$/% | 80.6 | 97.8 |
| $X_{tot}(CO)$/% | 99.2 | 99.7 |
| $X_{tot}(CO_2)$/% | 94.7 | 93.9 |
| $X_{tot}(CO_x)$/% | 97.9 | 97.8 |
| STY(MeOH)/ kg/(h litre$_{cat}$) | 0.98 | 1.15 |
| Recycle ratio | 3.5 | 0 |

The process according to the invention with a reactor with four reaction cells achieves a higher space-time yield of methanol by around 15% without recycling. More particularly, the $CO_2$ conversion per reactor pass is much higher than in the comparative example.

Optimization of the Process Conditions

The tables which follow indicate the effect of particular process parameters in the individual reaction cells in the heterogeneously catalytic synthesis of methanol from synthesis gas. The other process conditions correspond to those from the example shown in Table 2 (called Reference in Tables 3 to 5).

TABLE 3

Variation in the distribution of the catalyst volume

| | $V_{cat}$/m$^3$ | | | | | $X_{tot}(CO_x)$/ | STY(MeOH)/ |
|---|---|---|---|---|---|---|---|
| Case | 1st stage | 2nd stage | 3rd stage | 4th stage | total | % total | kg/(h I$_{cat}$) total |
| Reference | 8 | 8 | 8 | 8 | 32 | 95.1 | 1.53 |
| 1 | 4 | 6 | 10 | 12 | 32 | 92.1 | 1.49 |
| 2 | 12 | 10 | 6 | 4 | 32 | 96 | 1.56 |

TABLE 4

Variation in the cooling temperature $T_{cool}$ in the catalyst bed

| | $T_{cool}$/° C. | | | | $X_{tot}(CO_x)$/ | STY(MeOH)/ |
|---|---|---|---|---|---|---|
| Case | 1st stage | 2nd stage | 3rd stage | 4th stage | % total | kg/(h I$_{cat}$) total |
| Reference | 220 | 220 | 220 | 220 | 95.1 | 1.53 |
| 3 | 200 | 220 | 240 | 260 | 89.4 | 1.44 |
| 4 | 260 | 240 | 220 | 200 | 96 | 1.55 |

TABLE 5

Variation in the condensation temperature $T_{cond}$

| | $T_{cond}$/° C. | | | | Cooling output/ | $CO_2$ losses/ |
|---|---|---|---|---|---|---|
| Case | 1st stage | 2nd stage | 3rd stage | 4th stage | MW total | % total |
| Reference | 40 | 40 | 40 | 40 | 39.9 | 7.4 |
| 5 | 100 | 80 | 60 | 40 | 33.7 | 3.7 |
| 6 | 40 | 60 | 80 | 100 | 34.9 | 6.0 |

INDUSTRIAL APPLICABILITY

The invention proposes a reactor for conducting exothermic equilibrium reactions, especially for the performance of the methanol synthesis by heterogeneously catalysed conversion of synthesis gas, which enables readjustment and hence optimization of the reaction conditions along the longitudinal coordinate of the reactor, which, for example in the case of the methanol synthesis, leads to a reduction in the recycle ratio to smaller values as known in the case of use of the reactors known from the prior art. Corresponding recycle conduits, circulation compressors etc. can therefore have a smaller configuration, or it may be possible to dispense with them entirely. This reduces the corresponding capital costs.

The optimization of the reaction conditions along the longitudinal coordinate of the reactor also reduces the formation of unwanted by-products, which affords a purer target product and reduces the complexity of purification.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed.

Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS

[1] reactor
[2] reactor shell
[3] reaction cell
[10] conduit
[20] preheating zone
[22] conduit
[24] heat exchanger
[26] conduit
[28] conduit
[30] reaction zone
[31] catalyst bed
[32] conduit
[33] catalyst bed
[34] heat exchanger
[35] conduit
[36] conduit
[38] conduit
[40] first cooling zone
[42] conduit
[44] heat exchanger
[46] conduit
[47] conduit
[48] conduit
[50] second cooling and deposition zone
[51] deposition apparatus
[52] conduit
[53] conduit
[54] heat exchanger
[56] conduit
[60] conduit
[70] steam generator
[78] conduit

The invention claimed is:

1. A process for preparing methanol by converting a synthesis gas feed comprising hydrogen and carbon oxides, comprising the following process steps:
  (a) providing a reactor comprising at least two series-connected reaction cells that are in fluid connection with one another and are arranged in a common reactor shell, wherein each reaction cell comprises the following series-connected assemblies that are in fluid connection with one another:
  (aa) a preheating zone suitable for heating the feed mixture or the gaseous product stream from an upstream reaction cell, wherein the preheating zone can optionally be dispensed with in a first reaction cell in flow direction of the gaseous feed mixture;
  (ab) at least one reaction zone comprising a catalyst active in respect of the exothermic equilibrium reaction to be conducted and a cooling apparatus in a heat-exchanging relationship with the catalyst;
  (ac) at least one cooling zone comprising a cooling apparatus suitable for cooling the partly converted, gaseous product stream that has been laden with condensable reaction product and exits from the reaction zone to a temperature below the dew point of this gas;
  (ad) a deposition zone comprising a phase separation apparatus for separation of the product stream that exits from the cooling zone into a gaseous product stream that has been freed of condensate and a condensate stream comprising liquid reaction product;
  (ae) means of discharging the condensate stream comprising liquid reaction product and optionally means of feeding the condensate stream to a workup apparatus for the reaction product;
  (af) means of discharging the gaseous product stream that has been freed of condensate and means of feeding this gaseous product stream to a subsequent reaction cell arranged downstream or means of discharging the gaseous product stream from the process;
  (b) providing a synthesis gas feed comprising hydrogen and carbon oxides and introducing it into the reactor;
  (c) at least partly converting the synthesis gas feed in the reactor under methanol conversion conditions;
  (d) discharging a liquid reactor product stream comprising methanol and water from the reactor and optionally feeding the liquid reactor product stream to a further deposition apparatus and/or at least one further methanol workup apparatus; and
  (e) discharging a synthesis gas output stream and recycling this synthesis gas output stream to the reactor with a fixed recycle ratio and/or discharging the synthesis gas output stream from the process.

2. The process according to claim 1, wherein the recycle ratio is zero.

3. The process according to claim 1, wherein the amount of catalyst in the individual reaction zones (ab) of the individual reaction cells decreases in flow direction of the synthesis gas through the reactor.

4. The process according to claim 1, wherein the temperature of the cooling medium in the reaction zones (b) of the individual reaction cells is between 180 and 300° C., and remains the same or decreases in flow direction of the synthesis gas through the reactor.

5. The process according to claim 1, wherein the temperature of the cooling medium in the reaction zones (b) of the individual reaction cells is between 190 and 270° C., and remains the same or decreases in flow direction of the synthesis gas through the reactor.

6. The process according to claim 1, wherein the temperature of the cooling medium in the reaction zones (b) of the individual reaction cells is between 200 and 260° C., and remains the same or decreases in flow direction of the synthesis gas through the reactor.

7. The process according to claim 1, wherein the condensation temperature in the cooling zones of the individual reaction cells is between 20 and 120° C., and remains the same or decreases in flow direction of the synthesis gas through the reactor.

8. The process according to claim 1, wherein the condensation temperature in the cooling zones of the individual reaction cells is between 40 and 100° C., and remains the same or decreases in flow direction of the synthesis gas through the reactor.

9. The process according to claim 1, wherein a same heat carrier is used in all reaction cells and the temperature employed is the respective boiling point at different pressure levels and corresponding vapour temperatures.

10. The process according to claim 1, wherein all reaction cells are connected to a same steam generator and a heat carrier is provided in liquid form and undergoes at least partial evaporation in the region of the reaction cells.

11. The process according to claim 10, wherein the heat carrier is heat carrier oil or water.

* * * * *